United States Patent
Ford

Patent Number: 5,519,896
Date of Patent: May 28, 1996

[54] VENTILATED SPORT GOGGLES

[76] Inventor: Dan E. Ford, 2796 Lucas Turnpike, Accord, N.Y. 12404

[21] Appl. No.: 421,521

[22] Filed: Apr. 13, 1995

[51] Int. Cl.$^6$ ............................................ A61F 9/02
[52] U.S. Cl. ............................................ 2/436; 2/448
[58] Field of Search ........................ 2/426, 431, 435, 2/436, 437, 448, 449, 450, 451, 452, 454, 429, 430, 431, 434, 438, 439, 443, 447, 9, 424; 351/62

[56] References Cited

U.S. PATENT DOCUMENTS

| | | | |
|---|---|---|---|
| 613,186 | 10/1898 | Belt et al. | 2/447 |
| 2,296,634 | 9/1942 | Fink | 2/447 |
| 2,388,205 | 10/1945 | Bernheim et al. | 2/437 |
| 3,141,172 | 7/1964 | Hirschmann | 2/436 |
| 3,517,393 | 6/1970 | Beauchef | 2/436 |
| 3,708,224 | 1/1973 | Lindblom | 2/437 |
| 4,571,748 | 2/1986 | Carroll et al. | 2/436 |
| 4,649,577 | 3/1987 | Wiedner | 2/436 |
| 5,107,543 | 4/1992 | Hansen | 2/426 |
| 5,363,512 | 11/1994 | Grabos, Jr. et al. | 2/436 |

FOREIGN PATENT DOCUMENTS

| | | | |
|---|---|---|---|
| 522788 | 3/1956 | Canada | 2/436 |
| 1380221 | 1/1964 | France | 2/436 |
| 150848 | 9/1931 | Germany | 2/436 |
| 867431 | 7/1949 | Germany | 2/447 |

*Primary Examiner*—C. D. Crowder
*Assistant Examiner*—Michael A. Neas

[57] ABSTRACT

A pair of goggles for protecting and ventilating eyes of an individual. The inventive device includes a lens positionable over the individual's eyes. A mounting assembly is coupled to laterally opposed sides of the lens and is extendable about a head of an individual to secure the device relative thereto. Vent assemblies are directed through the lens and cooperate to circulate ram air between the lens and a wearer to preclude a formation of fog and moisture within the lens.

8 Claims, 3 Drawing Sheets

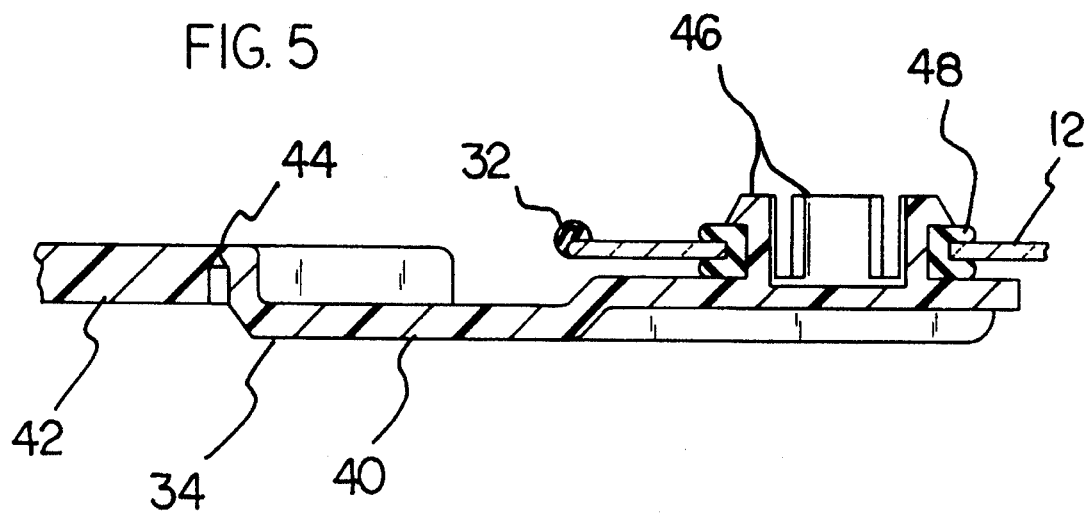
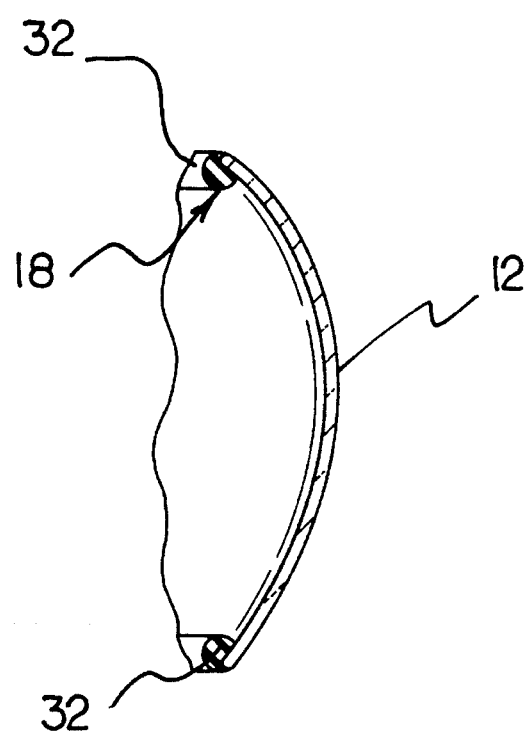

VENTILATED SPORT GOGGLES

BACKGROUND OF THE INVENTION

1. Field of the Invention

The present invention relates to eye covering devices and more particularly pertains to a pair of ventilated sport goggles for protecting and ventilating eyes of an individual.

2. Description of the Prior Art

The use of eye covering devices is known in the prior art. More specifically, eye covering devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art eye covering devices include U.S. Pat. No. 4,176,410; U.S. Pat. No. 4,741,611; U.S. Pat. No. 4,317,240; U.S. Pat. No. 4,150,443; U.S. Pat. No. Des. 285,020; and U.S. Pat. No. Des. 274,438.

While these devices fulfill their respective, particular objectives and requirements, the aforementioned patents do not disclose a pair of ventilated sport goggles for protecting and ventilating eyes of an individual which includes a lens positionable over the individual's eyes, a mounting means coupled to laterally opposed sides of the lens and extendable about a head of the individual, and vent means directed through the lens which cooperate to circulate ram air between the lens and the wearer to preclude a formation of fog and moisture within the lens.

In these respects, the pair of ventilated sport goggles according to the present invention substantially departs from the conventional concepts and designs of the prior art, and in so doing provides an apparatus primarily developed for the purpose of protecting and ventilating eyes of an individual.

SUMMARY OF THE INVENTION

In view of the foregoing disadvantages inherent in the known types of eye covering devices now present in the prior art, the present invention provides a new pair of ventilated sport goggles construction wherein the same can be utilized for protecting eyes of an individual. As such, the general purpose of the present invention, which will be described subsequently in greater detail, is to provide a new pair of ventilated sport goggles apparatus and method which has many of the advantages of the eye covering devices mentioned heretofore and many novel features that result in a pair of ventilated sport goggles which is not anticipated, rendered obvious, suggested, or even implied by any of the prior art eye covering devices, either alone or in any combination thereof.

To attain this, the present invention generally comprises a pair of goggles for protecting and ventilating eyes of an individual. The inventive device includes a lens positionable over the individual's eyes. A mounting assembly is coupled to laterally opposed sides of the lens and is extendable about a head of an individual to secure the device relative thereto. Vent assemblies are directed through the lens and cooperate to circulate ram air between the lens and a wearer to preclude a formation of fog and moisture within the lens.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new pair of ventilated sport goggles apparatus and method which has many of the advantages of the eye covering devices mentioned heretofore and many novel features that result in a pair of ventilated sport goggles which is not anticipated, rendered obvious, suggested, or even implied by any of the prior art eye covering devices, either alone or in any combination thereof.

It is another object of the present invention to provide a new pair of ventilated sport goggles which may be easily and efficiently manufactured and marketed.

It is a further object of the present invention to provide a new pair of ventilated sport goggles which is of a durable and reliable construction.

An even further object of the present invention is to provide a new pair of ventilated sport goggles which is susceptible of a low cost of manufacture with regard to both materials and labor, and which accordingly is then susceptible of low prices of sale to the consuming public, thereby making such pair of ventilated sport goggles economically available to the buying public.

Still yet another object of the present invention is to provide a new pair of ventilated sport goggles which provides in the apparatuses and methods of the prior art some of the advantages thereof, while simultaneously overcoming some of the disadvantages normally associated therewith.

Still another object of the present invention is to provide a pair of new pair of ventilated sport goggles for protecting and ventilating eyes of an individual.

Yet another object of the present invention is to provide a new pair of ventilated sport goggles which includes a lens positionable over the individual's eyes, a mounting means coupled to laterally opposed sides of the lens and extendable about a head of the individual, and vent means directed

3 through the lens which cooperate to circulate ram air between the lens and the wearer to preclude a formation of fog and moisture within the lens.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a cross sectional view taken along line 5—5 of FIG. 2.

FIG. 6 is a cross sectional taken along line 6—6 of FIG. 3.

DESCRIPTION OF THE PREFERRED EMBODIMENT

Figure 1:
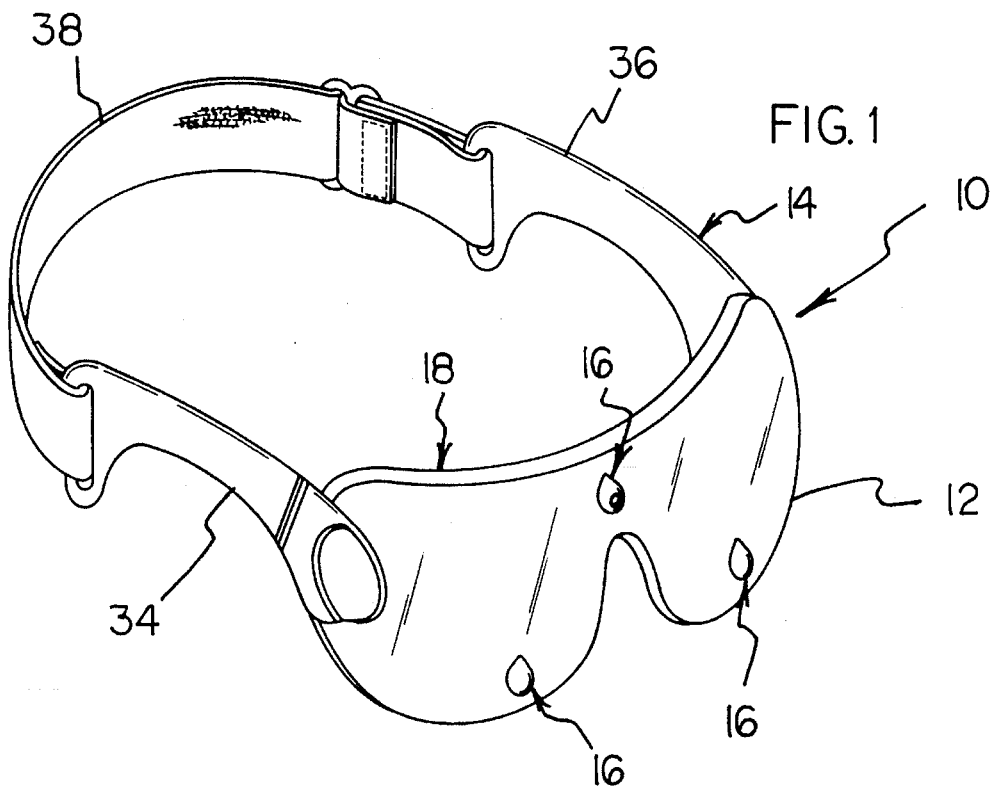
FIG. 1 is an isometric illustration of a pair of ventilated sport goggles according to the present invention in use.

With reference now to the drawings, and in particular to FIGS. 1–6 thereof, a new pair of ventilated sport goggles embodying the principles and concepts of the present invention and generally designated by the reference numeral 10 will be described.

More specifically, it will be noted that the pair of ventilated sport goggles 10 comprises a lens 12 of preferably unitary construction which is substantially translucent or transparent such that an individual may view items therethrough. The present invention 10 may further comprise mounting means 14 for securing the lens 12 over the eyes of a wearer. Vent means 16 are directed through the lens 12 for directing ram air into the lens 12 so as to preclude a formation or accumulation of fog and moisture within the lens 12. Sealing means 18 can be provided for circumferentially sealing a perimeter of the lens 12 to a face of the wearer. By this structure, an individual can effect protection and ventilation of his eyes as desired.

Figure 3:
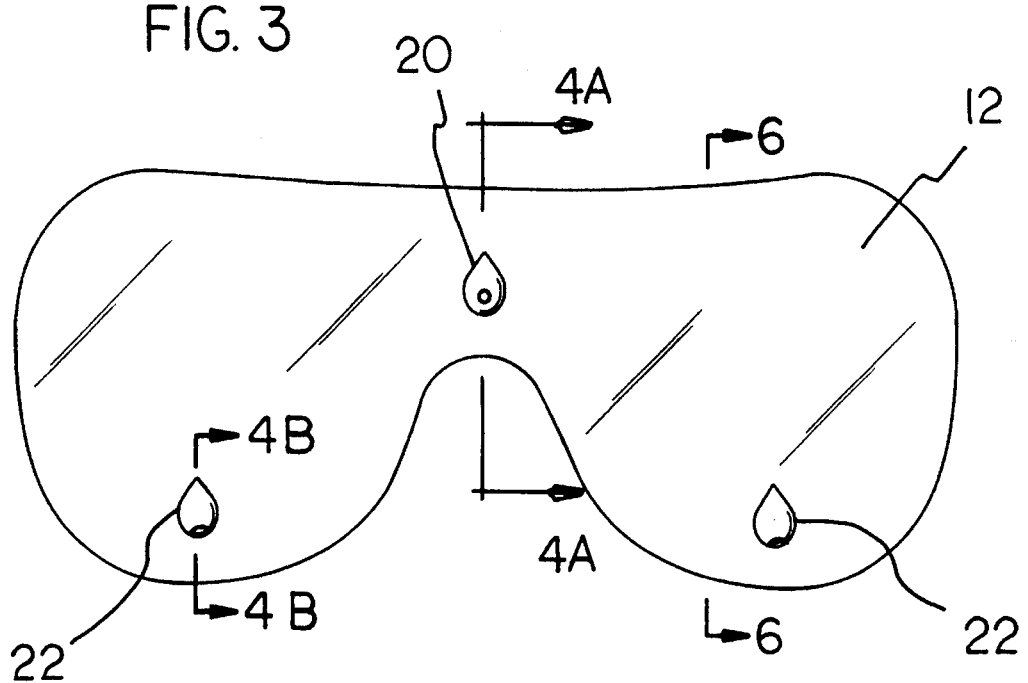
FIG. 3 is a front elevation view thereof.
Figure 4A:
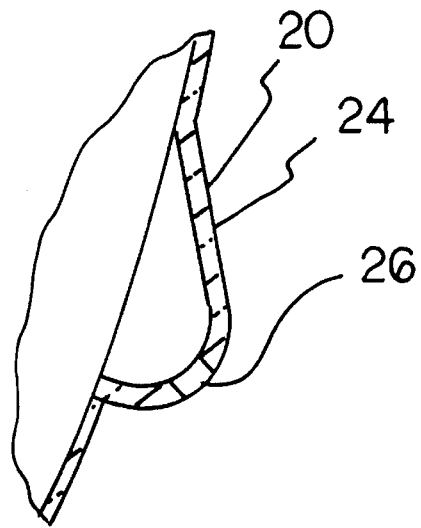
FIG. 4A is a cross sectional view taken along line 4A—4A of FIG. 3.
Figure 4B:
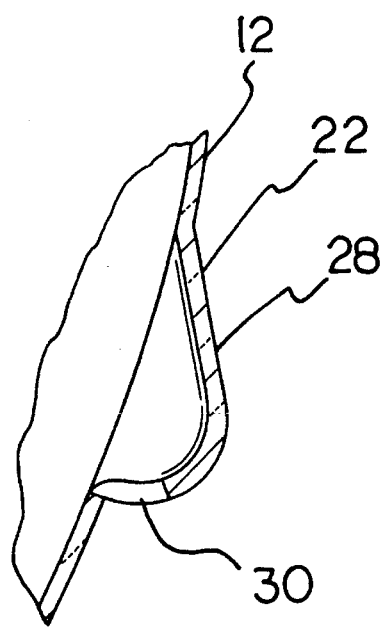
FIG. 4B is a cross sectional view taken along line 4B—4B of FIG. 3.

As best illustrated in FIGS. 3 through 4B it can be shown that the lens 12 is shaped so as to define an unlabeled first lens portion coupled to an unlabeled second lens portion by a reduced transverse dimensioned bridge portion. The bridge portion is centralized above a nose receiving aperture interposed between the lens portions for permitting projection of an individual's nose past the lens 12 when the same is positioned over the wearer's eyes.

With continuing reference to FIGS. 3 through 4B, it can be shown that the vent means 16 according to the present invention 10 preferably comprises an upper vent 20 for receiving ram air directed normally against the exterior surface of the lens 12, and at least one lower vent 22 for permitting egress of air from the lens 12 in direction substantially parallel to the exterior surface of the lens 12. Preferably, the vent means 16 includes a pair of lower vents 22, with each of the lower vents 22 being mounted to an individual one of the lens portions of the lens 12. As shown in FIG. 4A, the upper vent 20 preferably comprises an upper vent hollow projection 24 extending from the bridge portion of the lens 12. The upper vent hollow projection 24 is shaped so as to define an intake aperture 26 extending therethrough permitting direction of air through the upper vent hollow projection in a direction substantially orthogonally oriented relative to the exterior surface of the lens 12. In contrast, the lower vents 22, as shown in FIG. 4B, preferably each comprise a lower vent hollow project,on 28 projecting from the respective lens portion of the lens 12. The lower vent hollow projections 28 are each shaped so as to define an exit aperture 30 extending therethrough permitting egress of air from behind the lens 12 in a direction substantially parallel to the exterior surface of the lens. By this structure, ram air directed against the surface of the lens 12 will enter the upper vents 20 and exit through the lower vents 22 so as to circulate air behind the lens 12 to preclude a formation of fog and moisture within the lens.

As shown in FIG. 6, the sealing means 18 according to the present invention 10 preferably comprises an elastomeric perimeter seal 32 extending about an outer periphery of the lens 12. Preferably, the lens 12 is comprised of a substantially flexible material which can be caused to engage and conform to the topography of an individual's face, whereby the perimeter seal 32 of the sealing means 18 engages the individual's face so as to create a seal about the outer periphery of the lens 12 such that air is forced through the vent means 16 as described above.

Figure 2:
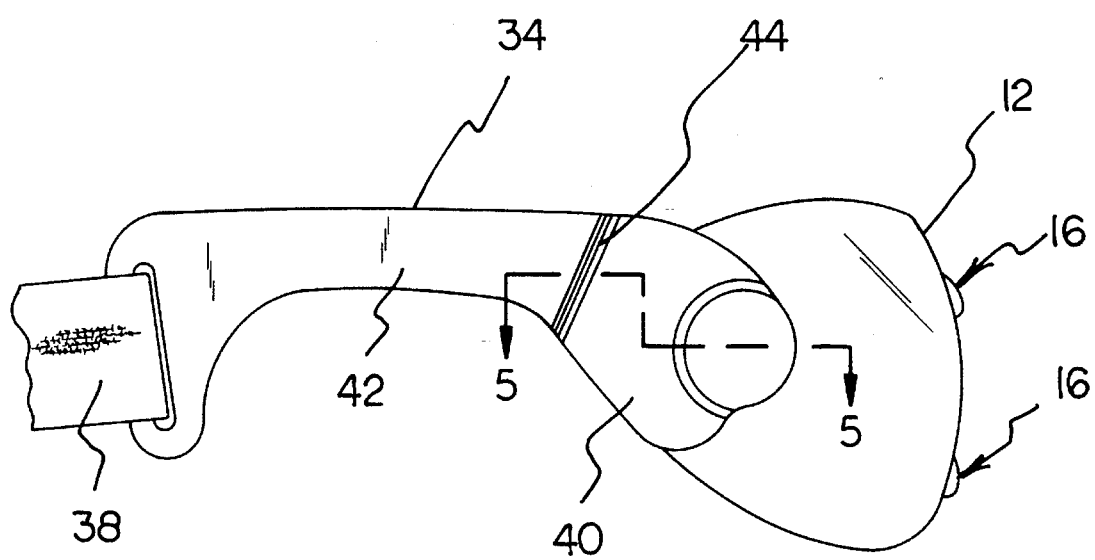
FIG. 2 is an enlarged side elevation view of the invention.

As best illustrated in FIGS. 2 and 5, it can be shown that the mounting means 14 according to the present invention 10 preferably comprises a first ear piece 34 pivotally mounted to a first side of the lens 12. A second ear piece 36 is similarly pivotally mounted to a second side of the lens 12, with an adjustable strap 38 extending between the first and second ear pieces. As shown in FIG. 2 for the first ear piece 34, each of the ear pieces 34 and 36 comprises a first portion 40 is pivotally mounted to the respective side of the lens 12. A second portion 42 is pivotally mounted to the first portion 40 by a hinge 44 interposed therebetween. Preferably, the hinge 44 comprises a living hinge integrally formed into the respective ear piece 34 or 36, as shown in FIG. 5 of the drawings. To pivotally mount the first portion 40 of the ear pieces 34 and 36 relative to the lens 12, a plurality of radially spaced tabs 46 project from an interior surface of the first portion 40 for extension through an unlabeled aperture formed in the lens 12. Preferably, a grommet 48 is interposed between the radially spaced tabs 46 and the lens 12 so as to create a seal which cooperates with the perimeter seal 32 so as to insure proper flow of air through the vents means 16. Thus, the radially spaced tabs 46 project through the aperture in the lens 12 so as to rotatably couple the respective ear piece 34 or 36 relative thereto. The radially spaced tabs 46, if desired, can be radially inwardly biased so as to permit selective separation of the ear piece 34 or 36 from the lens 12.

In use, the ventilated sports goggles according to the present invention 10 can be easily utilized for protecting and ventilating eyes of an individual. The specific structure and configuration of the vent means 16 operates to create a downward flow of air within the lens 12 as a result of ram air being directed against the vent means so as to preclude a formation of fog and moisture within the lens. The sealing means 18 operates to securely engage a perimeter of the lens 12 against the face of the individual to preclude an entrance of dirt and debris between the lens 12 and the individual's eyes. The mounting means 14 including the adjustable strap 38 and the pivotal portions 40 and 42 of the ear pieces 34 and 36 cooperate to permit the device 10 to be easily fitted and secured to a variety of individuals.

As to a further discussion of the manner of usage and operation of the present invention, the same should be apparent from the above description. Accordingly, no further discussion relating to the manner of usage and operation will be provided.

With respect to tile above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A ventilated sport goggles comprising:

a lens further comprising a first lens portion; a second lens portion; and a reduced transverse dimensioned bridge portion extending between the first and second lens portions comprised of a substantially flexible material which can be caused to engage and conform to a topography of an individual's face;

a vent means directed through the lens for directing ram air into the lens so as to preclude an accumulation of fog and moisture within the lens comprising an upper vent hollow projection extending from the bridge portion of the lens, the upper vent hollow projection being shaped so as to define an intake aperture extending therethrough permitting direction of air through the upper vent hollow projection in a direction substantially orthogonally oriented relative to an exterior surface of the lens, and at least one or more lower vents, with each of the lower vents being mounted to an individual one of the lens portions of the lens for permitting egress of air from the lens in direction substantially/parallel to an exterior surface of the lens;

a sealing means coupled to the lens for circumferentially sealing a perimeter of the lens to a face of a wearer comprising an elastomeric perimeter seal extending about an outer periphery of the lens.

2. The ventilated sport goggles of claim 1, wherein the lower vents each comprise a lower vent hollow projection extending from the respective lens portion of the lens, the lower vent hollow projections each being shaped so as to define an exit aperture extending therethrough permitting egress of air from behind the lens in a direction substantially parallel to an exterior surface of the lens.

3. The ventilated sport goggles of claim 1, and further comprising mounting means for securing the lens over eyes of a wearer.

4. The ventilated sport goggles of claim 3, wherein the mounting means comprises a first ear piece pivotally mounted to a first side of the lens; a second ear piece pivotally mounted to a second side of the lens; and an adjustable strap extending between the first and second ear pieces.

5. The ventilated sport goggles of claim 4, wherein the ear pieces each comprise a first portion pivotally mounted to the respective side of the lens; and a second portion pivotally mounted to the first portion.

6. The ventilated sport goggles of claim 4, wherein the ear pieces further comprise a living hinge interposed between the first and second portions.

7. The ventilated sport goggles of claim 6, wherein the first portion of each of the ear pieces includes a plurality of radially spaced tabs projecting from an interior surface of the first portion for extension through an aperture formed in the lens so as to pivotally mount the respective ear piece to the lens.

8. The ventilated sport goggles of claim 7, and further comprising a grommet interposed between the radially spaced tabs and the lens.

\* \* \* \* \*